United States Patent [19]
Allison et al.

[11] Patent Number: 5,075,042
[45] Date of Patent: Dec. 24, 1991

[54] SURFACTANT BLEND CONTAINING AN ALKYL POLY(ETHYLENEOXY)SULFONATE TO REDUCE DERMAL IRRITATION

[75] Inventors: William C. Allison, Uniontown; Louis J. Nehmsmann, Akron, both of Ohio

[73] Assignee: PPG Industries, Inc., Pittsburgh, Pa.

[21] Appl. No.: 610,714

[22] Filed: Nov. 6, 1990

Related U.S. Application Data

[63] Continuation of Ser. No. 345,388, May 1, 1989, abandoned.

[51] Int. Cl.$^5$ .................... C11D 1/12; C11D 1/14; C11D 1/22; C11D 1/29
[52] U.S. Cl. .................... 252/554; 252/547; 252/550; 252/551; 252/552; 252/558
[58] Field of Search .............. 252/535, 554, 531, 532, 252/533, 539, 540, 547, 548, 550, 551, 552, 558, 559, DIG. 5

[56] References Cited

U.S. PATENT DOCUMENTS

| | | | |
|---|---|---|---|
| 3,548,056 | 12/1970 | Elgen et al. | 424/171 |
| 3,793,233 | 2/1974 | Rose | 252/547 |
| 3,950,417 | 4/1976 | Verdicchio et al. | 252/545 |
| 4,186,113 | 1/1980 | Verdicchio et al. | 252/526 |
| 4,233,192 | 11/1980 | Lindemann et al. | 252/545 |
| 4,265,782 | 5/1981 | Armstrong et al. | 252/174.19 |
| 4,554,098 | 11/1985 | Klisch et al. | 252/547 |
| 4,612,142 | 9/1986 | Piorr | 252/555 |
| 4,759,875 | 7/1988 | Hart | 252/551 |
| 4,772,414 | 9/1988 | Marzec | 252/103 |
| 4,784,801 | 11/1988 | Hoeffkes | 252/554 |

FOREIGN PATENT DOCUMENTS

| | | | |
|---|---|---|---|
| 61-122750 | 3/1986 | Japan | 252/554 |
| 797119 | 6/1958 | United Kingdom | 252/551 |

OTHER PUBLICATIONS

Jacobs, Richard A., "Novel Anionic Sulfonates", *Soap/Cosmetics/Chemical Specialties*, Feb. 1987, pp. 41, 42 & 57.

Avanel S Surfactants-A New Family of Surfactants, bulletin published by PPG Industries, Inc., Nov. 1985, 8 pages.

*Primary Examiner*—Paul Lieberman
*Assistant Examiner*—Alexander G. Ghyka
*Attorney, Agent, or Firm*—Irwin M. Stein

[57] ABSTRACT

Described are detergent compositions that exhibit reduced skin irritation properties while providing excellent cleaning and detergent characteristics. The detergent composition contains anionic and/or nonionic surface active materials that are at least mildly irritating to the skin and an amount of alkyl poly(ethyleneoxy)-sulfonate sufficient to reduce the primary skin irritation potential of the detergent composition. The aliphatic poly(ethyleneoxy)sulfonate typically has a hydrophobe containing from 12 to about 22 carbon atoms and an average of from about 10 to about 30 ethyleneoxy groups, and is present in the detergent composition in amounts of from about 5 to about 50 percent of the total amount of surface active material in the detergent composition.

10 Claims, No Drawings

SURFACTANT BLEND CONTAINING AN ALKYL POLY(ETHYLENEOXY)SULFONATE TO REDUCE DERMAL IRRITATION

This application is a continuation of application Ser. No. 07/345,388, filed May 1, 1989, abandoned.

DESCRIPTION OF THE INVENTION

The present invention relates to detergent compositions that exhibit relatively low dermal irritation. More particularly, the present invention relates to liquid detergent compositions which provide excellent cleaning and detergency and which also exhibit reduced skin irritation properties.

Detergent compositions, like most types of cleaning agents, generally comprise a mixture of one or more primary surface active materials, i.e. surfactants, as the active ingredient. Surfactants normally used in such compositions, e.g., anionic and nonionic surfactants, have two moieties, i.e., (1) a hydrophobic hydrocarbon group miscible with organic materials and (2) a hydrophilic end group miscible with water. When an aqueous cleaning solution containing such a surfactant contacts a particle of soil on an object, the hydrocarbon group of the surfactant mixes with the soil particle and the hydrophilic end associates with the aqueous medium, thereby resulting in emulsification of the soil and its removal from the object carrying the soil.

Such detergent compositions have been used in various household cleaning compositions such as consumer dishwash liquids (light duty liquids), skin cleansers, cold water detergents, hard surface cleaners, hand soaps and in personal care products such as shampoos. During such use, various parts of the human anatomy, particularly the hands, come in direct contact with the cleaning composition. Commonly used anionic surfactants are irritating to the skin of mammals. Consequently, extensive contact thereof with the skin often results in noticeable redness and swelling of the skin. The quest for mild or milder cleaning systems, i.e. detergents which are non-irritating or minimally or only slightly irritating to the skin, has been ongoing for many years. Various approaches have been taken by the art to reduce skin irritation caused by surface active materials. For example, lotions have been employed to protect the skin. However, the protection afforded by such an approach has not been entirely effective.

It has now been discovered that incorporation of certain aliphatic poly(ethyleneoxy)sulfonates in detergent compositions, particularly liquid detergent compositions such as a light duty liquid, results in a detergent composition that exhibits a reduced level of skin irritation. Moreover, it has been found surprisingly that the aforesaid reduction in skin irritation effects is accomplished without sacrificing cleaning performance of the detergent composition. While not intending to be bound by any theory, it is believed that the aliphatic poly(ethyleneoxy)sulfonate, even at relatively low concentrations, functions as a counter-irritant to the more irritating anionic and/or nonionic surfactants commonly used in detergent compositions.

DETAILED DESCRIPTION OF THE INVENTION

Aliphatic poly(ethyleneoxy)sulfonates that may be used to reduce the skin irritation potential of anionic and/or nonionic surfactants, e.g., sodium lauryl sulfate, may be represented by the general formula:

$$RO(C_2H_4O)_{n-1}CH_2CH_2SO_3M$$

wherein R may be a branched and/or straight chain, saturated or unsaturated, aliphatic hydrocarbon group containing from about 12 to about 22 carbon atoms, e.g., from about 12 to about 18 carbon atoms, more particularly, from about 12 to about 15 carbon atoms. When the aliphatic poly(ethyleneoxy)sulfonate is synthesized from aliphatic alcohols, R may be a mixture of aliphatic hydrocarbon groups, the mixture depending on the particular manufacturer of the precursor aliphatic alcohol. In a typical embodiment, R is a branched and/or straight chain saturated hydrocarbon group.

The letter "n" in the foregoing general formula, i.e., the number of ethylene oxide units, designates the average number of moles of ethylene oxide present per mole of aliphatic poly(ethyleneoxy)sulfonate and hence may be less than a whole number. In the present embodiment, n may be a number between about 10 and about 30, e.g., from about 12 to about 20, preferably about 15. M is typically an alkali metal such as sodium or potassium and more typically is sodium.

The above-described aliphatic poly(ethyleneoxy)sulfonates are known in the art and may be readily prepared by chlorination, e.g., with thionyl chloride, of the corresponding ethoxylated aliphatic alcohol, and subsequent conversion of the resulting chloride to the sulfonate with sodium sulfite. Ethoxylated aliphatic alcohols such as linear alkyl ethoxylated alcohols are commercially available. Certain of such aliphatic poly(ethyleneoxy)sulfonates are commercially available from Mazer Chemicals, a unit of PPG Industries, Inc., as AVANEL ® S Anionic Surfactants.

The above-described aliphatic poly(ethyleneoxy)sulfonates are themselves non-irritating or only minimally irritating to the skin; however, it has been found from the evidence at hand that such sulfonates mitigate and reduce the dermal irritation effects of the more irritating anionic surfactants, such as sodium lauryl sulfate, even when the total amount of the more irritating surfactant remains constant. Hence, it has been surprisingly found that the described aliphatic poly(ethyleneoxy)sulfonate functioned as a counter-irritant. This function was observed even at relatively low concentrations of the aliphatic poly(ethyleneoxy)sulfonate in the detergent composition.

The amount of aliphatic poly(ethyleneoxy)sulfonate required to provide a detergent composition exhibiting a reduced level of dermal irritation is an amount sufficient to reduce the primary skin irritation potential of the detergent composition, i.e., the composition without the aliphatic poly(ethyleneoxy)sulfonate. Such amount may be termed a counter-irritating amount and will commonly represent between about 5 and about 50 weight percent of the total amount of active surfactant in the detergent composition. The amount of active surfactant in a detergent formulation is typically about 20 weight percent. More typically, the aliphatic poly(ethyleneoxy)sulfonate will be present in amounts of from about 10 to about 35, e.g., 15-20, weight percent of the total amount of active surfactant in the detergent composition. In a more preferred embodiment, the weight ratio of the aliphatic poly(ethyleneoxy)sulfonate surfactant to the other more irritating surface active materials in the composition is about 1:5.

The detergent compositions of the present invention may be readily prepared by methods known in the art for preparing liquid and solid compositions, e.g., by admixing with agitation the individual detergent ingredients with the amount of water or other aqueous medium used in the composition. The aliphatic poly(ethyleneoxy)sulfonate ingredient of the detergent composition may be incorporated into the composition along with and in the same manner as the other surface active ingredients.

As described, many anionic and/or nonionic surfactants typically used in detergent compositions are irritating to the skin of mammals. The irritant effects of such surfactants are commonly determined by the guidelines described by 40 CFR 798.4470. As defined therein, "Dermal irritation" is the production of reversible inflammatory changes in the skin following the application of a test substance. Such changes are the characteristic redness and swelling of the skin as a result of direct prolonged contact of the skin and the surfactant. Dermal irritation is commonly scored and reported as a mean primary irritation score having values ranging from 0.00 to 8.00, as described in J. Soc. Cosmet. Chem., Vol. 13, No. 6, 1962, pages 281-289. Substances which are non-irritating, minimally irritating or only slightly irritating generally have primary irritation scores of less than about 1.50. Substances which have primary irritation scores greater than 1.50 are more irritating—the higher the score the more irritating the substance. Such substances may be termed mildly irritating (1.51-3.00), moderately irritating (3.01-5.00), severely irritating (5.01-6.50) or extremely irritating (6.51-8.00), depending on the score.

While the aliphatic poly(ethyleneoxy)sulfonates described herein may be used with any anionic and/or nonionic surfactant commonly used in detergent compositions, the counter irritating benefits provided by such sulfonates are most readily observed when used with anionic and/or nonionic surfactants which exhibit a primary skin irritation value of at least 1.50 on the aforesaid scale, which are commonly known as Draize values.

Anionic surfactants that may be used in the detergent compositions of the present invention include, without limitation, alkyl sulfates, alkyl ether sulfates, alpha olefin sulfonates, alkyl monoglycerylether sulfonates, alkyl monoglyceride sulfates, alkyl monoglyceride sulfonates, alkyl sulfonates, e.g., secondary alkane sulfonates, alkylaryl sulfonates, alkyl sulfosuccinates, alkylamido sulfosuccinates, alkylethoxy sulfosuccinates, and acyl isethionates among others. More particularly, alkyl sulfates such as sodium lauryl sulfate may be represented by the formula, $R_1—CH_2—OSO_3X$; alkyl ether sulfates such as ammonium lauryl ether sulfate may be represented by the formula, $R_1(OCH_2CH_2)_p—OSO_3X$; alkyl monoglycerylether sulfonates may be represented by the formula, $R_1OCH_2CH(OH)—CH_2—SO_3X$; alkyl monoglyceride sulfates may be represented by the formula, $R_1COOCH_2CH(OH)—CH_2OSO_3X$; alkyl monoglyceride sulfonates may be represented by the formula, $R_1COOCH_2CH(OH)—CH_2SO_3X$; alkyl sulfonates may be represented by the formula, $R_1SO_3X$; alkylaryl sulfonates may be presented by the formula, $R_1PhSO_3X$; alkylsulfosuccinates may be represented by the formula, $R_1—CH_2—O—C(O)—CH(SO_3X)—CH_2—C(O)—OX$; alkylamido sulfosuccinates may be represented by the formula $R_1—C(O)—N(R')CH_2CH_2O—C(O)—CH(SO_3X)—CH_2—C(O)—OX$; alkylethoxy sulfosuccinates may be represented by the formula, $R—(OCH_2CH_2)_q—O—C(O)—CH(SO_3X)—CH_2—C(O)—OX$; and acylisethionates may be represented by the formula, $R_1—C(O)O—CH_2CH_2SO_3X$; wherein $R_1$ is an alkyl group having from about 8 to about 18 carbon atoms, R' is hydrogen or ethyleneoxy, i.e., ($—CH_2CH_2O—$), Ph is the aromatic bivalent phenyl group, p is an integer of from about 2 to 6, q is an integer of from about 1 to 10, and X is a member selected from the group consisting of alkali metal ions, alkaline earth metal ions and ammonium ions.

The anionic surface active materials most commonly used in detergent compositions are alkyl sulfates, alkyl ether sulfates, alpha olefin sulfonates and alkylaryl sulfonates.

Nonionic surfactants that may be used to prepare detergent compositions are typically water-soluble polyoxyethylene derivatives of a hydrophobic base, amine oxides and alkyl alkanolamides. Such polyoxyethylene derivatives may be a member of the group consisting of:

a. The reaction products of 9-20 carbon atom fatty acid monoesters of aliphatic polyhydric alcohols, which polyhydric alcohols contain at least 3 hydroxyls, with at least 10 moles of ethylene oxide;

b. The reaction products of 9-20 carbon atom alcohols, acids and mercaptans with at least two-thirds as many ethylene oxide units as the number of carbon atoms in the hydrophobic base;

c. The reaction products of 12-24 carbon atom alkylphenols and alkylcylohexanols with at least as many ethylene oxide units as the number of carbon atoms in the hydrophobic base; and d. Block copolymers of propylene oxide and ethylene oxide.

Alkyl alkanolamides may be represented by the formula, $R_2C(O)NH_s(CH_2CH_2OH)_{2-s}$, wherein $R_2$ is typically a $C_{12}-C_{18}$ alkyl and s is 0 or 1.

The preferred type of nonionic surfactant used in detergent compositions are those from group (a) described above, e.g. polyoxyethylene sorbitan monolaurates, particularly those having about 20 polyoxyethylene moieties, i.e., those commonly called polyoxyethylene(20) sorbitan monolaurate.

The method of the present invention may be used to prepare detergent compositions, whether solid or liquid, useful in various applications such as personal care, household and industrial applications. More particularly, such detergent compositions include: consumer liquid dishwash detergents (light duty liquids); cold water wash detergents; liquid hard surface cleaners; liquid soaps or cleansers for cleaning mammals, e.g., the human body or other mammals, inanimate objects and the like; hand soap bars, e.g., synthetic detergent bars commonly referred to as Syndet bars; and lotions.

In addition to the surface active material, the detergent composition may contain one or more of the following: thickeners, dyes, perfumes, preservatives, pH adjusters, fillers, carriers, conditioners, opacifiers, emollients and the like.

The detergent composition commonly also contains an inert liquid medium, e.g., solvent, such as water and/or water miscible solvents. Water miscible solvents are typically low molecular weight hydroxyl-containing solvents such as the low molecular weight alcohols, which are preferably of the monohydric or polyhydric saturated aliphatic type. Examples of such alcohols include: ethyl alcohol, propyl alcohol, isopropyl alcohol, n-butyl alcohol, ethylene glycol, propylene glycol, glycerol (glycerine), etc. Alcohols possessing ether linkages may also be used, i.e., monomethylether of ethylene glycol, monoethylether of ethylene glycol, diethylene glycol, etc. Preferably, the inert liquid medium is selected from water, aliphatic monohydric alcohols, dihydric alcohols of about 2 to 4 carbon atoms, lower alkyl ethers of dihydric alcohols and mixtures thereof.

The present invention is more particularly described in the following examples which are illustrative only since numerous modifications and variations therein will be apparent to those skilled in the art. Percentages are by weight unless specified otherwise.

EXAMPLE 1

Commercially available sodium lauryl sulfate (30 percent active), sodium $C_{12}$-$C_{15}$ Pareth-15 sulfonate (AVANEL® S-150 anionic surfactant) and a 50—50 blend of the sodium lauryl sulfate and the Pareth-15 sulfonate were evaluated for potential primary dermal irritation using six New Zealand white rabbits. The back of each rabbit was clipped with an electric clipper on the day prior to dosing. The test surfactant was topically applied to two non-abraded dorsal test sites per rabbit (0.5 ml per site). The test sites were wrapped with semi-occlusive binders immediately after dosing. The binders were removed four hours post-dose administration and the exposure sites gently wiped with gauze to remove as much non-absorbed test surfactant as possible. Dermal irritation was evaluated at 4.5, 28, 52 and 76 hours as well as 4, 7, 10 and 14 days post dose administration. Erythema and edema were scored separately accordingly to the Draize method found in Table I of 40 CFR 798.4470. The mean primary dermal irritation score for each of the surfactants tested are tabulated in Table I.

TABLE I

| SURFACTANT | MEAN PRIMARY DERMAL IRRITATION SCORE |
|---|---|
| 1. Sodium Lauryl Sulfate (30% Active) | 2.33 |
| 2. AVANEL® S-150 (25% Active)* | 0 |
| 3. 50/50 Blend of 1 and 2 | 0.69 |

*Sodium linear alkyl poly(ethyleneoxy)sulfonate having an average of 15 ethyleneoxy groups and alkyl groups of from 12 to 15 carbon atoms.

The data of Table I shows that sodium lauryl sulfate scored a 2.33, which is classified as mildly irritating while the AVANEL® S-150 did not register a response and thus was scored a 0, which is classified as non-irritating. The 50/50 blend of the two surfactants had a score of 0.69, which is classified in the category of only slightly irritating. The reduction in dermal irritation potential of the 50—50 blend compared to the neat sodium lauryl sulfate was by a factor of over 70 percent, which is considerably more than would be expected as a result of simple dilution.

EXAMPLE 2

Surfactant formulations were prepared utilizing the sodium lauryl sulfate of Example 1 and an AVANEL® S-150 anionic surfactant having 25 percent actives. The compositions are described in Table II. Each of the surfactant compositions were evaluated for potential primary dermal irritation using six New Zealand white rabbits in accordance with the procedure described in Example 1 except that the test surfactants were applied to three separate intact test sites on each rabbit. The mean primary dermal irritation score for each test surfactant composition is tabulated in Table II.

TABLE II

| SAMPLE NO. | 1 | 2 | 3 |
|---|---|---|---|
| Composition | | | |
| Deionized Water | 0 | 25 | 50 |
| AVANEL® S-150 (25%) | 50 | 25 | 0 |
| Sodium Lauryl sulfate (30%) | 50 | 50 | 50 |
| Mean Primary Dermal Irritation Score | 1.0 | 0.78 | 2.72 |

The data of Table II shows that a 50/50 mixture of water/sodium lauryl sulfate produced an irritation score of 2.72 and addition of 25 and 50 parts of AVANEL® S-150 thereto (with a corresponding decrease in the water content) decreased the dermal irritation score to 0.78 and 1.0 respectively. Thus, a small amount of the sodium alkyl poly(ethyleneoxy)sulfonate surfactant decreased the irritation score by a factor of about 3 in compositions where the amount of sodium lauryl sulfate was kept constant.

EXAMPLE 3

In accordance with the procedure of Example 2, further surfactant compositions were prepared using the sodium lauryl sulfate of Example 1 and the sodium alkyl poly(ethyleneoxy)sulfonate (AVANEL® S-150) of Example 2. Each of the compositions were evaluated for potential primary dermal irritation in the manner described in Example 1, except that the test surfactants were applied topically to four separate intact test sites on the shaved surface of each rabbit. The surfactant compositions and mean primary dermal irritation scores for each composition are tabulated in Table III.

TABLE III

| SAMPLE NO. | 1 | 2 | 3 | 4 |
|---|---|---|---|---|
| Composition | | | | |
| Deionized Water | 25.0 | 38.0 | 48.3 | 47.1 |
| AVANEL® S-150 (25%) | 25.0 | 12.0 | 10.0 | 17.6 |
| Sodium Lauryl sulfate (30%) | 50.0 | 50.0 | 41.7 | 35.3 |
| Mean Primary Dermal Irritation Score | 0.67 | 0.67 | 0.78 | 0.45 |

The data of Table III shows that the addition of AVANEL® S-150 to sodium lauryl sulfate, even in small amounts, produced dermal irritation scores significantly lower than those obtained with neat sodium lauryl sulfate.

EXAMPLE 4

Light duty liquids (LDL) having the formulations found in Table IV were prepared and together with a commercially available consumer dishwash liquid were evaluated for potential primary dermal irritation in a manner similar to that described in Example 1. LDL Sample 2 is the control formulation and is similar in composition and performance to the consumer dishwash liquid product tested. The formulation of Sample 1 is the same as Sample 2 except that a portion of of the total anionic solids has been replaced with AVANEL® S-150. The total anionic actives level remain about the same in Samples 1 and 2, and the amount of anionics (other than the AVANEL® S-150) relative to each other also remain the same. Considering the alcohol ether sulfate and the alkylarylsulfonic acid salt in the formulation, Sample 2 contains a total anionic activity of about 30 percent. The ratio of sulfate vs sulfonate in Samples 1 and 2 was kept constant as was all other ingredients in the system.

Each of the test LDL liquids and the consumer dishwash liquid were applied topically to two separate sites, (one intact and one abraded site) on the shaved surface of each rabbit. Each test site was occluded for four hours following dose administration. Dermal irritation was scored at 0.5, 24, 48 and 72 hours, and at 4 and 7 days after binder removal. The mean primary dermal irritation score for each test LDL was based on the 24, 48 and 72 hour readings and are tabulated in Table IV.

TABLE IV

| Sample No. | 1 | 2 |
|---|---|---|
| Composition | | |
| Water | 27.05 | 34.33 |
| Triethanolamine | 1.6 | 1.92 |
| Dodecyl Benzene Sulfonic Acid | 3.6 | 4.32 |
| Alfonic ® 1412-A$^a$ (60% solids) | 33.4 | 40.08 |
| Mazox ®LDA$^b$ | 10.0 | 10.0 |
| Magnesium Chloride | 1.0 | 1.0 |
| Ammonium Xylene Sulfonate | 1.5 | 1.5 |
| AVANEL ® S-150 (35% solids) | 15.0 | — |
| d-Limonene, Grade M | 0.6 | 0.6 |
| Ethanol | 6.25 | 6.25 |
| Mean Primary Dermal Irritation Score | 0.67 | 3.20 |
| Mean Primary Dermal Irritation Score for Commercial Consumer Dishwash Liquid was 4.30 | | |

$^a$Ammonium alkyl ethoxy sulfate
$^b$Lauryl dimethyl amine oxide

Table IV shows nearly a five-fold reduction in primary skin irritation potential by the addition of the AVANEL ® S-150 anionic surfactant to the composition of Sample 2. Thus, the composition containing the alkyl poly(ethyleneoxy)sulfonate had an irritation score of 0.67 which is classified as only slightly irritating whereas the formulation without the alkyl poly(ethyleneoxy)sulfonate and the commercial consumer dishwash liquid had significantly greatly dermal irritation scores, which scores (3.20 and 4.30 respectively) are classified as moderately irritating.

The LDL compositions of Samples 1 and 2 were evaluated against national branded products using C.S.M.A. Soil "A" in test method DCC-10, Foam Stability of Hand Dishwashing Detergents published by the Chemical Specialties Manufacturers Association, in 0 and 150 ppm hardness water. The results (22-24 dishes washed for each) indicated that the formulations of Samples 1 and 2 were essentially equal in performance to each other and to the national branded products. The soil composition was as follows:

| C.S.M.A. Soil "A" | |
|---|---|
| Ingredient | Weight % |
| Lard (not hydrogenated) | 18.3 |
| Wesson Oil | 9.2 |
| Corn Oil (Mazola) | 9.2 |
| Oleic Acid (USP) | 4.2 |
| Salt | 0.4 |
| Gelatin (Knox) | 0.4 |
| Flour (Gold Medal) | 41.6 |
| Water | 16.7 |

| -continued | |
|---|---|
| C.S.M.A. Soil "A" | |
| Ingredient | Weight % |
| | 100.0 |

While the present invention has been exemplified with respect to certain embodiments thereof, it is to be understood that the invention is not intended to be limited to such details except as and insofar as they appear in the appended claims.

What is claim is:

1. In detergent composition with anionic surfactant as the primary surface active material, said anionic surfactant being selected from the group consisting of alkyl sulfates represented by the formula $R_1-CH_2-OSO_3X$, alkyl ether sulfates represented by the formula, $R_1(OCH_2CH_2)_p-OSO_3X$, alkylaryl sulfonates represented by the formula, $R_1PhSO_3X$, wherein $R_1$ is an alkyl group having form about 8 to about 18 carbon atoms, Ph is the aromatic bivalent phenyl group, p is an integer of from about 2 to 6, and X is a member selected from the group consisting of alkali metal ions, alkaline earth metal ions and ammonium ions, and mixtures of such anionic surfactants, and wherein said anionic surfactant is a skin irritant having a mean primary skin irritation potential of at least 1.5, the improvement wherein the detergent composition contains in combination an amount of aliphatic poly(ethyleneoxy)sulfonate sufficient to serve as a counter-irritant to said anionic surfactant and thereby reduce the primary skin irritation potential of the detergent composition, said aliphatic poly(ethyleneoxy)sulfonate being represented by the general formula, $$RO(C_2H_4O)_{n-1}CH_2CH_2SO_3M,$$

wherein R is a $C_{12-22}$ hydrocarbon group, n is a number between 10 and 30 and M is an alkali metal, and representing from about 5 to about 50 weight percent of the total amount of active surfactant in the detergent composition.

2. The detergent composition of claim 1 wherein R is a $C_{12-18}$ hydrocarbon group, n is a number between 12 and 20, and M is sodium or potassium.

3. The detergent composition of claim 2 wherein R is a $C_{12-15}$ hydrocarbon group and n is about 15.

4. The detergent composition of claim 1 wherein the aliphatic poly(ethyleneoxy)sulfonate represents from about 10 to about 35 weight percent of the total amount of surface active material in the detergent composition.

5. The detergent composition of claim 2 wherein the aliphatic poly(ethyleneoxy)sulfonate represents from about 10 to about 35 weight percent of the total amount of surface active material in the detergent composition.

6. The detergent composition of claim 5 wherein R is a $C_{12-15}$ hydrocarbon group and n is about 15.

7. The detergent composition of claim 6 wherein the aliphatic poly(ethyleneoxy)sulfonate represents from about 15 to about 20 weight percent of the total amount of surface active material in the detergent composition.

8. The detergent composition of claim 2 wherein the weight ratio of aliphatic poly(ethyleneoxy)sulfonate to other surface active materials in the composition is about 1:5, R is a $C_{12}-C_{15}$ hydrocarbon group, n is about 15 and M is sodium.

9. The detergent composition of claim 5 wherein the detergent is a light duty liquid.

10. The detergent composition of claim 2 wherein the weight ratio of aliphatic poly(ethyleneoxy) sulfonate to other surface active materials in the composition is about 1:5.